United States Patent [19]

Smith

[11] Patent Number: 5,958,394

[45] Date of Patent: Sep. 28, 1999

[54] SHAVING COMPOSITIONS HAVING QUALITIES OF PRE-SHAVE LUBRICATION, POST-SHAVE SKIN CONDITIONING AND BLADE LIFE EXTENSION

[76] Inventor: Earl Smith, 7 Flint Dr., Delmar, N.Y. 12054

[21] Appl. No.: 09/040,951

[22] Filed: Mar. 18, 1998

[51] Int. Cl.⁶ ................................................. A61K 7/15
[52] U.S. Cl. .................. 424/73; 424/401; 424/195.1; 424/74; 514/844
[58] Field of Search .............................. 424/73, 74, 401, 424/195.1; 514/844

[56] References Cited

U.S. PATENT DOCUMENTS

| | | | |
|---|---|---|---|
| 3,824,303 | 7/1974 | Lanzet et al. | 424/47 |
| 3,949,067 | 4/1976 | Gibbs | 424/73 |
| 4,978,529 | 12/1990 | Denick, Jr. | 424/195.1 |
| 5,294,438 | 3/1994 | Chang et al. | 424/73 |
| 5,387,412 | 2/1995 | Moore | 424/73 |
| 5,587,156 | 12/1996 | Wdowik | 424/73 |

OTHER PUBLICATIONS

Union Carbide Corp. Material Safety Data Sheet "Polyox Water Soluble Resins" dtd. Jan. 23, 1997.

*Primary Examiner*—Thurman K. Page
*Assistant Examiner*—James M. Spear
*Attorney, Agent, or Firm*—Fredric T. Morelle

[57] ABSTRACT

A shaving preparation aid with ingredients for lubricating the skin, extending razor edge life and post-shave skin conditioning. A basic water-alcohol mix is further combined with an edible, dietary or otherwise soluble or wetable mucilate, preferably psyllium fiber, to realize, in this fundamental form, a combination sufficient to achieve the aforesaid properties. Other substances are disclosed such as polyether(s), vitamin E (tocopherol), glycerol, lecithin and perfumes that, in combination with the basics, serve to promote one property over the others or add more aesthetic character to the invention. The compositiors are applied to the skin as both pre- and post-shave conditioners, as well as to the blade edge for preservation.

5 Claims, No Drawings

SHAVING COMPOSITIONS HAVING QUALITIES OF PRE-SHAVE LUBRICATION, POST-SHAVE SKIN CONDITIONING AND BLADE LIFE EXTENSION

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates generally to water-based shaving aids which are used primarily to lubricate the skin in preparation for shaving with a blade. More particularly, this invention eclipses aids that presently exist by possessing two additional qualities: (1) it is a highly effective skin conditioner; and, (2) for post-shaving storage, it is applied to the razor blade in order to prolong keenness of the blade edge.

2. Description of Related Art

Modern shaving compositions are devised to provide several features that are meant to aid and enhance the comfort and effectiveness of blade edge shaving. Two of the most ancient aids are water and oil, such as olive oil or animal fat. It is apparent that, throughout shaving history, shaving aids have improved to feature different additives such as beard softeners, perfumes, improved lubricants, surfactants, humectants, moisturizers and, in this century, bacteriostats and the many aerosols/propellants which foster better foaming or delivery.

U.S. Pat. No. 5,294,438 ('438), issued to Chang et al. discloses several shaving compositions that contain a host of additives and which are subjected, along with several prior art compositions, to slide (incline) tests in order to objectively test lubricity qualities. The patent presents several mixtures that have from about ten to about 15 ingredients. The slide tests are staged by comparing the patentee's composition to many well known shaving creams/gels. In the '438 disclosure, the salient ingredients, along with a water "phase", are: a water insoluble thermoplastic polymeric elastomer and an emollient oil in an oil to elastomer ratio, from about 5 to 1 to about 20 to 1, that comprises 95% of the formulation (by weight). The remaining 5% appears as soap/detergent. It is a shaving lather in that it contains a soap or detergent, as well as an oil phase and makes no pretense to any blade life extension capability.

Moore, in U.S. Pat. No. 5,387,412 ('412), discloses only a method for using the humectant propylene glycol as a pre-shave conditioner. It is employed in aqueous solution of at least 50% to not more than 80% glycol, above which the hydrating property diminishes.

Gibbs, in U.S. Pat. No. 3,949,067 ('067), shows the use of a different humectant, namely vinegar and lemon juice, mixed with an oil, tocopherol, that is applied directly to the razor blade. This is not an extender of blade life, but rather a topical (blade) lubricant. It would appear that, if allowed to remain on the blade, say for storage, the organic acids present in this humectant would soon corrode the fine blade edge.

Lanzet et al., U.S. Pat. No. 3,824,303 ('303), show the use of alcohol diester compounds for electric shaving, pre-shave skin lubrication only. The elements are water, alcohol and a diester (oil). These ingredients are combined with a propellant and are applied as a foam to the skin. Since they serve to lubricate the razor heads, they may prevent corrosion, but are not proposed as (wettable) razor blade life extenders or skin conditioners.

Final to the relevant art thus far discussed, Wdowik, U.S. Pat. No. 5,587,156 ('156) proposes, as blade-supporting additives for shaving compositions, solid water-insoluble particulates. The distinctiveness of this product appears to reside in the size of the particles that are used, because silica gel, used extensively in products ranging from tooth paste to shaving creams, may also be described as water-insoluble particulate matter. In addition to the solid particulates, of varying types, the '156 compositions include emollients, water, surfactants, etc., as mentioned above.

Digressing from the genre thus far discussed, it is relevant to address a class of substances known as dietary mucilates, particularly those containing natural mucilate, such as certain gelatinous or mucilaginous fibers and proteins, e.g., cereal brans, seed husks and gelatin. The fibers, like the proteins, possess varying degrees of water solubility, slipperiness and gelatinous mass formability (when mixed with water). This slippery character can also be acquired, for heretofore unused shaving applications, by use of vegetable and animal proteins. Relative to the use of dietary fibers, as will be hereinafter disclosed, there appears to be little, if any, mention of their use beyond the field of general health and nutrition. One such fiber is psyllium. U.S. Pat. No. 4,978,529 ('529), for example, presents a composition having milled/unmilled blond psyllium seed husk which provides, in its mucilaginous portion, the laxative psyllium (psyllium hydrophilic mucilloid). All uses presented therein, and throughout the prior art, are dietary related and consumed for health benefits. The '529 disclosure is most relevant in its showing of how the powdered psyllium seed husk can be rendered hydrophilic by admixing with an alcohol and triacetin. The necessity of such processing is avoided, however, because the desired psyllium product: is readily available on supermarket or health store shelves.

3. Incorporation by Reference

U.S. Pat. Nos. 5,587,156, 5,294,438 and 4,978,529 are hereby incorporated by reference for their disclosures of nonsoluble particulate additives, polymeric additives and inculcation of psyllium properties, preparation and known uses, respectively.

BRIEF SUMMARY OF THE INVENTION

Two unique features are added to a shaving preparation aid to supplement its beard-softening and lubrication utilities—one to extend razor edge life and another to condition the skin before, during and after shaving, that is, to include enhanced humectant properties for moisture conservation and skin conditioning. The enhanced humectant property is dualistic in that there is also acquired a lubricity that may be revitalized, during shaving, by lightly rewetting the skin.

Basically, a water-alcohol mix is further mixed with a non-toxic, wettable (or soluble) organic fiber, preferably dietary psyllium. In this fundamental form there is realized a sufficient formulation that achieves the aforesaid properties and novel improvements; however, other substances are disclosed that, in combination with the basics, serve to promote one of the skin conditioning, lubricating or blade life extending properties over the others and/or add more aesthetic character to the invention.

Other organic lubricants are disclosed such as plant or animal proteins, but their use is not pursued rigorously in this teaching.

BRIEF DESCRIPTION OF THE SEVERAL VIEWS OF THE DRAWINGS

Not Applicable

DETAILED DESCRIPTION OF THE INVENTION

The art relating to wet shaving is replete with varied blade devices and shaving aids that are intended to make shaving more comfortable but, because of the common use of soaps or detergents, provide little skin moisture retention or replacement. Moreover, and irrespective of the use of higher grade materials in razor blade manufacture, there still remains the problem of blade edge deterioration due to corrosion. It has also become the custom to apply to the shaved skin, some form of a moisture-conserver (termed a "humectant") and/or a moisture replacement (a "moisturizer").

The instant invention has the basic qualities first mentioned above while additionally providing, in a single composition, a rewettable pre-shave lubricant, a post-shave ungent (a humectant cum moisture replacement) and a metal-protective dressing which, when applied to the blade edge before storage, prevents the rapid blade edge deterioration that is so characteristic in the art.

Two ingredients are used, one not seen before in the art, which grant to the invention its unique properties: a rewettable lubricant-humectant in the form of a natural, organic fiber; and a water-soluble resin, a polyether. The former, an organic fiber, is better characterized as a soluble or wettable dietary fiber such as a cereal bran or a natural plant mucilloid, containing a natural mucilate such as found in many botanical/vegetable (and even animal) substances. For example, many mucilaginous substances such as mucic acid derivatives, gums such as guar gum and proteins such as albumin and gelatin have been considered, but abandoned in favor of the dietary fibers because the latter are readily available, are not overly water-retentive and are produced economically.

1. Definitions

Throughout this disclosure, use of the terms "mucilate" and "fiber", means those natural botanical/vegetable, but not necessarily non-animal, substances that have a slippery or mucilaginous character when in a liquid phase; and, "wettable" means generally having a hydrophilic character.

2. Compositions

The fiber psyllium, used in the instant invention has been described in the incorporated '529 patent and was selected, as was the polyether, poly(oxyethylene)/poly(ethylene oxide), for the specific properties discussed above, as well as their non-toxicity storability. The compositions being hereinafter disclosed were developed empirically, and only after multiple experiments were conducted using other emollients and mucilaginous carbohydrates/proteins The first of the compositions (collectively "CM") which achieved the invention's desired properties consisted in an aqueous alcohol and mucilate mixture. For the specific mixture, iso-propanol was chosen over ethanol for its economy and availability, the latter being equally suitable. This mixture is designated CM1 and is comprised of about 92%–93% pure water, about 6%–7% iso-propyl alcohol, and about 1.0% psyllium (in hydrophilic or soluble state) or an equivalent mucilate. The proper balance of psyllium was coarsely defined by tactile sense, it being required, throughout the invention's development, that this lubricant-humectant be slippery upon its (wet) application to the skin and at the (several) possible rewettings during the shaving process. Further to this definition, the final, skin-conditioning application of CM1 must dry on the skin to a clear, non-shiny coating. Thus, the operational aspects of the invention must be balanced with the aesthetic.

The second composition CM2, supplements CM1 with a polyether, poly(oxyethylene)/poly(ethylene oxide) $[(CH_2CH_2O)_x]$, in an amount from 0.05%–0.1% by weight; the water-alcohol constituency varying as 92%–93% and 6%–7%, respectively. This soluble resin is considered non-toxic at this titer. Use of the polyether is made to advance the slickness feature, when drawing a blade across the wetted or liquid-soaped skin; but only a minute titer can be used or the blade shearing capability may be severely diminished.

The third, CM3, departs from the nearly same titers of CM2 by the addition of about 2.0%–2.5% lecithin by weight. Lecithin, added for the emollient "feel", is also observed to slow evaporation of the water-alcohol mix, necessitating an alteration in the weight percentages of the remaining ingredients to: water, about 82%–83%; iso-propanol, about 14%–15%; psylliun/mucilate, about 0.6%–0.8%; and, the polyether, about 0.02%–0.025%.

Also considered is a CM3 derivative class termed CM3 Plus (or CM3+). CM3+ contains, in addition to psyllium at about 0.8% to about 0.9% and a polyether at about 0.005% to about 0.007%, aloe vera, glycerol, Vitamin E (tocopherol) or lecithin at weight percentages ranging from about 0.3% to about 1.0%. The balance is composed of the water-alcohol mixture having a water content of about 95% to 98% which is a ratio of about 11:1. Any other ingredients known in the art may, from time to time be used, so long as there is no departure from the basic constituencies shown herein.

3. Methodology

CM1 through CM3+ enjoy, as a single aid, application by the same method; but, offer differing results when used with varying brands of shaving lathers (soaps) and equipment (razors). For example, if certain brands of foam lather are used, the formulation with the polyether is observed to work best. Overall best results have been obtained using either single or double bladed apparatus with good grades of liquid hand and face soaps. Soaps that are antiseptic or bacteriostatic are well suited for use with this invention. It has been observed that certain foaming lathers have a tendency to clog a multibladed razor; when such a lather is used, the instant compositions incorporating a polyether, or suitable lubrication enhancement, of known type, is indicated.

Beginning with the pre-shaving methodology, one pre-soaks the area to be shaved which, for the remainder of this disclosure, will be referred to as facial hair or, simply, the "beard." This soaking consists of a persistent wetting with warm water (110–120° F.) over a period of about 30 seconds. Immediately afterward, the CM compound of choice is applied sparingly over the entire beard area to be shaved. Depending on its particular constituency, i.e., the alcohol/water/humectant contents, too heavy an application may prolong drying time and unduly protract the shaving process. As soon as the CM has dried, it is lightly coated with the shaving soap and the shaving routine is begun.

The shaving routine commences with a blade that has been treated by applying to it a drop or two of the CM aid/compound, in a wiping motion from the rear to, and over, the blade edge. Next, normal shaving is accomplished. Thereafter, reshaving any or all of the shaving area is preceded by a light rewetting. The latter routine may be repeated several times until the desired closeness of shave is attained. The shaved area should then be washed and towel-dried.

Routines after shaving, for which the CM's (the invention's) formulations are best adapted, consist of post-shave conditioning application for the skin and protectant application for the blade edge. Immediately after drying the skin, a sparing amount of the CM aid is reapplied to the shaved and cleansed area. The blade is carefully rinsed, wiped dry and the coating process with the CM aid, as practiced prior to applying the blade (above paragraph), is repeated. Once air-dried, the blade is stored normally.

The preceding methods have been tested by the inventor and several test subjects. Greater ease of shaving, without any form of injury such as cutting or razor/chemical irritation, was reported throughout the test phases. The tests for effect on blade life were more objective, in that blade lives, as observed by the several test subjects, were clearly extended by 100% to 150% over those of the same brands of blades used in the subject's former daily shaving routines. Blade edges were examined and showed no corrosion, as would have been expected using them in the former routines.

The compositions set forth herein present a smaller range of constituents than seen generally in the art. Absence of soap or detergent was a strived-for quality, as was the unique character of rewettability. Other ingredients may be substituted, within their generic classes, for those employed here without departing from the spirit of this invention; that spirit is constrained only by the appended claims.

What is claimed is:

1. A shaving aid for rewettable lubrication of skin during shaving, conditioning said skin after shaving and for applying to a razor blade edge to preserve its keeness during storage, said aid effecting a dryable and rewettable composition comprising a first amount of a water-alcohol mixture, at least one alcohol of said mixture selected from the group consisting of ethanol and propanol in a water:alcohol weight ratio of from about 16:1 to about 11:1 and at least one edible organic mucilate, said mucilate selected from the group consisting of cereal bran, guar gum and hydrophilic psyllium in a second amount of from about 0.5% to about 1.0% by weight of said aid and effective for imparting to the skin a slippery, light wetness which air-dries to a smooth, non-shiny clearness.

2. The aid of claim 1 wherein there is added a third amount of a water-soluble resin of from about 0.05% to about 0.1% by weight with the balance being said water-alcohol mixture having a water:alcohol weight ratio of about 14:1.

3. The aid of claim 2 wherein said third amount of said resin is a polyether of from about 0.02% to about 0.25% by weight $(CH_2CH_2O)_x$ and there is further added a fourth amount of lecithin in a weight of from about 0.6% to about 0.8%.

4. The aid of claim 1 wherein said second amount of the mucilate is from about 0.5% to about 1.0% by weight, and there are added: a polyether in a weight of from about 0.005% to about 0.007%; a fourth amount of lecithin in a weight of from about 2.0% to about 2.5%; and, the balance is said water-alcohol mixture in a water:alcohol weight ratio or about 11:1.

5. The aid of claim 4 further comprising from about 0.1% to about 1.0% by weight of each of aloe vera, glycerol, tocopherol and lecithin.

* * * * *